(12) United States Patent
Bouchet et al.

(10) Patent No.: US 6,353,108 B1
(45) Date of Patent: Mar. 5, 2002

(54) METHOD FOR PREPARING 4-(3-PYRIDINYL)-1H-IMIDAZOLE AND THE INTERMEDIATES USED

(75) Inventors: Raphael Bouchet, Le Pre Saint Gervais; Jacques Lagouardat, Noisy le Grand; Jacques Scholl, Romainville, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/743,562

(22) PCT Filed: Jul. 8, 1999

(86) PCT No.: PCT/FR99/01649

§ 371 Date: Jan. 26, 2001

§ 102(e) Date: Jan. 26, 2001

(87) PCT Pub. No.: WO00/02875

PCT Pub. Date: Jan. 20, 2000

(30) Foreign Application Priority Data

Jul. 9, 1998 (FR) .............................. 98 08796

(51) Int. Cl.$^7$ ..................... C07D 401/04; C07D 213/04
(52) U.S. Cl. ..................... 546/274.1; 546/334; 546/336
(58) Field of Search .............................. 546/274.1, 334, 546/336

(56) References Cited

U.S. PATENT DOCUMENTS 4,302,464 A    11/1981   La Mattina et al.

FOREIGN PATENT DOCUMENTS

FR    1259360       3/1961
JP    02145572   *   6/1990   ................. 546/334

OTHER PUBLICATIONS

La Mattina et al "Use of . . . Acetals", Synthesis, No. 4, 1980 pp. 329–330.

* cited by examiner

Primary Examiner—Charanjit S. Aulakh
(74) Attorney, Agent, or Firm—Bierman, Muserlian and Lucas

(57) ABSTRACT

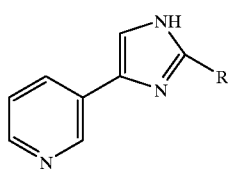

(I)

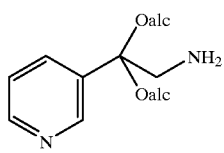

(II)

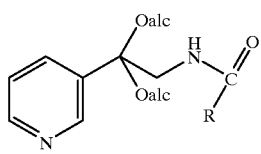

(IV)

The invention concerns a method for preparing compounds of formula (I) wherein R represents a hydrogen atom or an allyl radical containing up to 8 carbon atoms, characterised in that it consists in subjecting a compound of formula (II) wherein alc represents the residue of an alkyl radical containing up to 4 carbon atoms to the action of a compound of formula (III): $RCONH_2$, wherein R retains its previous meaning, to obtain the compound of formula (IV) wherein R retains its previous meaning which is subjected to cyclization to obtain the desired product of formula (I).

10 Claims, No Drawings

METHOD FOR PREPARING 4-(3-PYRIDINYL)-1H-IMIDAZOLE AND THE INTERMEDIATES USED

This application is a 371 of PCT/FR99/01649 filed Jul. 8, 1999.

The present invention relates to a process for the preparation of 4-(3-pyridinyl)-1H-imidazole, of certain of its derivatives as well as the intermediate products used.

A subject of the invention is a process for the preparation of compounds of formula (I)

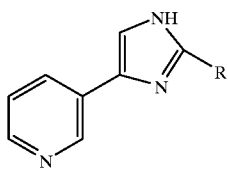

(I)

in which R represents a hydrogen atom or an alkyl radical containing up to 8 carbon atoms characterized in that a compound of formula (II)

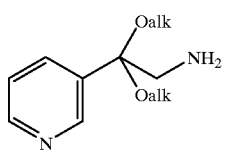

(II)

in which alk represents the remainder of an alkyl radical containing up to 4 carbon atoms is subjected to the action of a compound of formula (III)

 (III)

in which R retains its previous meaning, in order to obtain the compound of formula (IV)

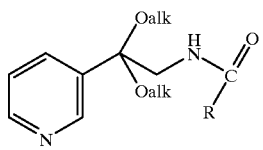

(IV)

in which R retains its previous meaning which is subjected to a cyclization in order to obtain the sought product of formula (I).

When R represents an alkyl radical, it is for example the methyl, ethyl, n-propyl, isopropyl, n-butyl, isobutyl or ter-tbutyl radical.

Alk represents for example a methyl, ethyl or n-propyl radical.

In a preferred embodiment, the reaction between the compounds (II) and (III) takes place in a mixture of alcohol and formamide. As alcohol there can be mentioned methanol, ethanol or propanol.

The cyclization of the compound of formula (IV) takes place in formamide.

A more particular subject of the invention is the preparation of the compound of formula (I) in which R is a hydrogen atom.

A more particular subject of the invention is a process characterized in that alk represents a methyl radical.

The cyclization preferably takes place by heating.

4-(3-pyridinyl)-1H imidazole is a known product described for example in J. Chem.-Soc.-753–5 1938 which can be used for preparing pharmaceutical products (cf. EP 680967).

A subject of the invention is also a process characterized in that the product of formula (II) is prepared by the action of an alcohol and of an alkaline alcoholate, $alk_1OH/alk_2OM$, $alk_1$ and $alk_2$, identical or different, representing an alkyl radical containing up to 4 carbon atoms and M representing a sodium or potassium atom on a compound of formula (A),

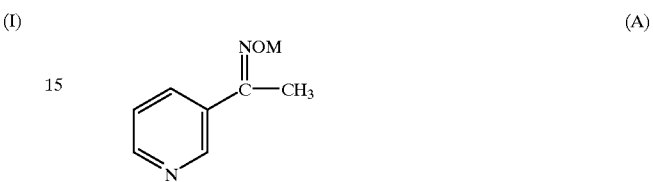

(A)

OM representing a hydroxyl radical blocked, in the form of a good parting group in order to obtain 3-(2H-azirin-3-yl) pyridine

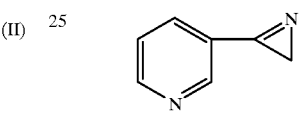

which is subjected to the action of an acid in the presence of an alcohol alkOH, alk retaining the same meaning as previously in order to obtain the corresponding compound of formula (II)

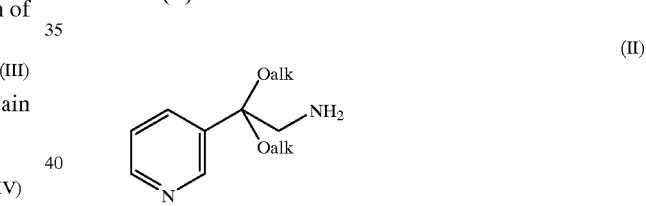

(II)

The oxime is protected for example in the form of mesylate or tosylate, the alcohol and the alkaline alcoholate are for example methanol and sodium methylate, ethanol and sodium ethylate, butanol and sodium terbutylate.

The acid used can be oxalic acid, formic acid or also hydrochloric or sulphuric acid.

In a preferred embodiment:
M is a tosyl radical
methanol is used in the presence of sodium methylate
the acid is oxalic acid.

A more particular subject of the invention is a process in which alk, $alk_1$ and $alk_2$ represent the same alkyl radical for example the methyl radical.

A more particular subject of the invention is a process in which the intermediate product 3-(2H-azirin-3-yl)-pyridine is not isolated.

A more particular subject of the invention is a process characterized in that 1-(3-pyridinyl)-ethanone O-[(4-methylphenyl) sulphonyl] oxime is subjected to the action of methanol and sodium methylate in order to obtain 3-(2H-azirin-3-yl)-pyridine which is subjected to the action of oxalic acid in order to obtain β,β-dimethoxy-2-(3-pyridinyl) ethyl)-amine which is subjected to the action of formamide in order to obtain N-[β,β-dimethoxy-2-(3-pyridinyl)ethyl]- formamide which is subjected to a cyclization in order to obtain the sought product.

A quite particular subject of the invention is a process in which the intermediate products used are not isolated.

The compounds of formula (II) with the exception of β,β-diethoxy-3-pyridine ethanamine described in Org. Synth. (1986) 64, 1926 are new products and are in themselves a subject of the present invention.

The compounds of formula (IV) are new and are in themselves a subject of the present invention.

A more particular subject of the invention is the compounds of formula (II) and (IV) described in the experimental part namely:

β,β-dimethoxy-3-pyridine ethanamine and N-[β,β-dimethoxy-2-(3-pyridinyl)ethyl]-formamide.

The following examples illustrate the invention without however limiting it.

Preparation: β,β-dimethoxy-3-pyridine ethanamine

Stage A: 3-[2H-azirin-3-yl]-pyridine 100 g of 1-(3-pyridinyl)-ethanone O-[(4-methylphenyl) sulphonyl]-oxime is introduced at 20° C. under a nitrogen atmosphere into a solution containing 400 ml of anhydrous methanol and 23.45 g of sodium methylate. Agitation is carried out for 2 hours at 20–22° C. and a suspension containing the sought product is obtained.

Stage B: β,β-dimethoxy-3pyridine ethanamine

The suspension obtained previously is cooled down to 0° C. and 31.03 g of oxalic acid is added. Agitation is carried out for 15 minutes at 0°/+5° C. A suspension is obtained which is used as it is in Example 1. After isolation and purification, β,β-dimethoxy-3-pyridine ethanamine is obtained.

NMR CDCl$_3$ ppm 1.03(broad m) assumed mobile NH$_2$ 3.02(s)

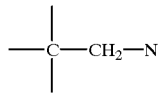

3.22(s) 6H 2 OCH$_3$
7.33(bdd, J=5 and 9) H$_5$
7.80(dt, J=9 and 2) H$_4$
8.59(dd, J32 5 and 2) H$_6$
8.73(dd, J=2 and 1) H$_2$

EXAMPLE 1

4-(3-pyridinyl)-1H-imidazole

Stage A$_1$: N-[β,β-dimethoxy-2-(3-pyridinyl)ethyl]-formamide 100 ml of formamide is added at 60° C. to the suspension prepared above. In this way a suspension is obtained which is used as it is in the following stage. After separation and purification the sought product is obtained.

Stage A$_2$: 4-(3-pyridinyl)-1Himidazole 7.2 g of β,β-dimethoxy-3-pyridineethanamine in 15 ml of formamide is heated for 5 hours at 80° C. under nitrogen.

The reaction mixture is maintained under agitation at 20° C. for 16 hours. In this way the sought product is obtained.

(Yield=51%).

NMR CDCl$_3$ ppm
3.24(s) 3.26(s) 6H 2 CH3O
3.55(d, s after exch.) CH$_2$—NHCO
3.75(d, s after exch.) CH$_2$—NHCO
5.80(m) mobile H
8.21(m) mobile H
7.32(m) H5
7.64(d, s after exch.) N—CHO
8.00(d, s after exch.) NH—CHO
7.75 to 7.82(m) H$_4$
8.54(dd) 8.57(dd) H$_6$
8.68(m) 8.70(dd) H$_2$ Stage B: 4-(3-pyridinyl)-1H-imidazole The suspension obtained in Stage A is heated at 125° C. while distilling the methanol. The reaction medium is maintained under agitation for 16 hours. A suspension is obtained which is cooled down to 80° C. and 400 ml of demineralized water is added. 130.3 g of oxalic acid is added at 80° C. After cooling down to 60 ° C., agitation is carried out for 1 hour at 60° C., followed by cooling down to 20° C., agitating for 1 hour at 20° C., cooling down to 0° C., agitating for 16 hours at 0° C., separating and washing. In this way the oxalate of the sought product is obtained. 4-(3-pyridinyl)-H-imidazole is obtained by the action of a solution of potash.

NMR CDCl$_3$ ppm
7.38 (dd, J=5 and 8) H$_5$
7.78(bs) 7.80(bs) H$_2$' H$_5$'
8.12(bd, J=8) H$_4$
8.41(dd,J=2 and 5) H$_6$
9.03(bs) H$_2$
12.36(broad m) mobile H

What is claimed is:

1. A process for the preparation of a compound of the formula

I wherein R is hydrogen or alkyl of 1 to 8 carbon atoms comprising reacting a compound of the formula

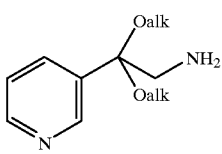

II wherein alk are individually alkyl of 1 to 4 carbon atoms with a compound of the formula

RCONH$_2$    III to obtain a compound of the formula

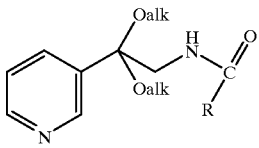
IV and subjecting the latter to cyclization to obtain a compound of formula I.

2. The process of claim 1 wherein R is hydrogen.
3. The process of claim 1 wherein alk is methyl.
4. The process of claim 1 wherein the cyclization is effected by heating.
5. A process for the preparation of a compound of the formula

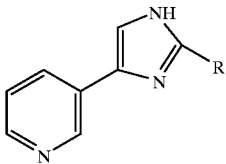
I wherein R is hydrogen or alkyl of 1 to 8 carbon atoms comprising reacting a compound of the formula

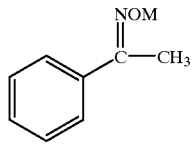
A wherein M is a hydroxy protective group with an alcohol and an alcoholate of the formula $alk_1OH$ and $alk_2OM'$ $alk_1$ and $alk_2$ are individually alkyl of 1 to 4 carbon atoms and M' is sodium or potassium to form 3-(2H-azirin-3-yl)-pyridine, reacting the latter without isolation with an acid to form a compound of formula

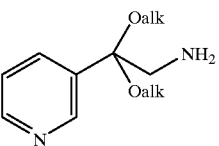
II reacting the latter without isolation with a compound of the formula $RCOHN_2$   III to obtain a compound of the formula

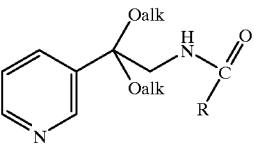
IV and subjecting the latter to cyclization to obtain a compound of formula I.

6. The process of claim 5 wherein $alk_1$, $alk_2$ are methyl.
7. The process of claim 5 wherein M is tosyl.
8. The process of claim 5 wherein the compound of Formula IV is not isolated.
9. The process of claim 5 wherein 1-(3-pyridinyl)-ethanone-O-[(4-methylphenyl)-sulfonyl]-oxime is reacted with methanol and sodium methylate to form 3-(2H-azirin-3-yl)-pyridine, reacting the latter without isolating it with oxalic acid to obtain β,β-dimethyloxy-3-pyridine-ethanamine, reacting the latter without isolating it with formamide to obtain N-[β,β-dimethoxy-2-(3-pyridinyl)-ethyl]-formamide and subjecting the latter without isolating it to cyclization by heating to obtain a compound of formula I.
10. The process of claim 5 wherein cyclization is effected by heating.

* * * * *